United States Patent [19]

Blum et al.

[11] Patent Number: 4,888,124

[45] Date of Patent: Dec. 19, 1989

[54] PREPARATION OF STABLE DISPERSIONS OF FINELY DIVIDED POLYISOCYANATES AND PREPARATION OF HEAT-CROSSLINKABLE ISOCYANATE SYSTEMS

[75] Inventors: Rainer Blum; Horst Belde, both of Ludwigshafen; Rolf Osterloh, Gruenstadt; Guenter Uhl, Worms, all of Fed. Rep. of Germany

[73] Assignee: BASF Aktiengesellschaft, Ludwigshafen, Fed. Rep. of Germany

[21] Appl. No.: 112,049

[22] Filed: Oct. 23, 1987

Related U.S. Application Data

[63] Continuation of Ser. No. 863,033, May 14, 1986, abandoned.

[30] Foreign Application Priority Data

May 14, 1985 [DE] Fed. Rep. of Germany ....... 3517333

[51] Int. Cl.$^4$ .......................... C09K 3/00; H05B 33/00
[52] U.S. Cl. .................................. 252/182.2; 524/44; 524/49; 524/52; 524/68
[58] Field of Search .................. 528/44, 52, 49; 252/182.2

[56] References Cited

U.S. PATENT DOCUMENTS

| | | |
|---|---|---|
| 3,236,895 | 2/1966 | Lee ........................ 564/505 |
| 3,428,592 | 2/1969 | Youker ................... 260/29.2 |
| 3,654,370 | 4/1972 | Yeakey ................... 564/480 |
| 3,655,627 | 4/1972 | Hutzler et al. ......... 260/77.5 |
| 3,893,956 | 7/1975 | Brandt .................... 524/211 |
| 4,029,626 | 6/1977 | Gillemot et al. ....... 260/31.6 |
| 4,068,086 | 1/1978 | Dalibor .................. 560/169 |
| 4,224,417 | 9/1980 | Hajek et al. ........... 521/166 |
| 4,331,778 | 5/1982 | Summerfeld et al. ... 521/129 |
| 4,383,068 | 5/1983 | Brandt .................... 524/196 |
| 4,386,218 | 5/1983 | Rasshofer et al. ..... 564/38 |
| 4,400,497 | 8/1983 | Blum et al. ............ 528/45 |
| 4,418,160 | 11/1983 | Rasshofer et al. ..... 521/159 |
| 4,483,974 | 11/1984 | Grogler et al. ........ 528/68 |
| 4,507,456 | 3/1985 | Blum et al. ............ 528/45 |
| 4,525,570 | 6/1985 | Blum et al. ............ 528/75 |
| 4,667,008 | 5/1987 | Grogler et al. ........ 528/44 |

FOREIGN PATENT DOCUMENTS

| | | |
|---|---|---|
| 2639491 | 2/1978 | Fed. Rep. of Germany . |
| 2640295 | 9/1978 | Fed. Rep. of Germany . |
| 1466708 | 3/1967 | France . |
| 848671 | 9/1960 | United Kingdom . |
| 874430 | 8/1961 | United Kingdom . |
| 878542 | 10/1961 | United Kingdom . |
| 994900 | 6/1965 | United Kingdom . |
| 1033912 | 6/1966 | United Kingdom . |

OTHER PUBLICATIONS

Kunststoff-Handbuch, Bd. VII, Polyurethane (1966), S. 11 ff M. Hartmann, R. Dowbenko, U. T. Hockswender: "Organic Coating Applied Polymer Science", 46 1982, S. 429–432.
High & Polymers, vol. XVI, "Polyurethane, Chemistry & Technology", N.Y. London Bd. I, 1962, Sn 32–42, S. 44–54., Bd. II, 1964, S. 5–6, S. 198–199.
Kunststoff-Handbuch VII, Munchen, 1966 (Vieweg--Hochtlen, Carl-Hanser Verlag) S 45–71.

*Primary Examiner*—Harold D. Anderson
*Assistant Examiner*—Dennis R. Daley
*Attorney, Agent, or Firm*—Keil & Weinkauf

[57] ABSTRACT

A process for the preparation of stable dispersions of finely divided polyisocyanates, and the preparation of heat-crosslinkable isocyanate systems.

Stable dispersions of finely divided polyisocyanates in a liquid which may or may not contain surfactants, protective colloids and other assistants are obtained by a method in which polyisocyanates are treated with a stabilizer in the presence of absence of the liquid, and the dispersions prepared from these are finely dispersed and/or milled under the action of high shear forces, if necessary with the addition of further stabilizer.

These dispersions are useful as crosslinking agents, particularly for the preparation of heat-cross-linkable isocyanate systems.

8 Claims, No Drawings

PREPARATION OF STABLE DISPERSIONS OF FINELY DIVIDED POLYISOCYANATES AND PREPARATION OF HEAT-CROSSLINKABLE ISOCYANATE SYSTEMS

This application is a continuation of application Ser. No. 863,033, filed on May 14, 1986, now abandoned.

The present invention related to a process for the preparation of stable dispersions of finely divided polyisocyanates in a liquid by treating polyisocyanates with stabilizers, wherein the polyisocyanates dispersed in the liquid and treated with the stabilizer are finely dispersed and/or milled under the action of high shear forces, and the preparation of heat-crosslinkable isocyanate systems.

Because of their good reactivity, polyisocyanates have become very important for many applications, for example for adhesives, sealants and decorative and protective coatings on many hard and flexible substrates, and for the production of particle boards and compact and foamed synthetic materials.

However, considerable difficulties are encountered in that the members of the isocyanate groups react with the intended reactants, e.g. polyols or polyamines, at as low as room temperature, i.e. it is not possible to formulate combinations that are stable during storage.

To overcome these difficulties, two-component systems are frequently used. In this case, the reactants are stored as separate formulations and only mixed directly before application, after which the reaction takes place spontaneously or is accelerated by heat and/or a catalyst.

An example of such a material is described in U.S. Pat. No. 4,029,626. The disadvantages of this process are the necessity of preparing and storing the two components separately, the difficulties with regard to exact metering and thorough mixing prior to application and the danger of blocking the mixer and applicator through premature reaction.

Another known method for the preparation of polyisocyanate materials which are stable during storage starts from uncrosslinked prepolymers which contain only a small amount of free isocyanate, atmospheric moisture serving as the crosslinking agent. This method is described in, for example, French Pat. No. 1,237,936. The disadvantages in this case are that curing starts at the surface and proceeds only very slowly into the depth of the coating, the final properties are achieved only after weeks or months and, for example, curing does not take place at all between large surfaces or in cavities.

It is also possible to formulate stable systems if the polyisocyanates are first reacted with a monofunctional reactant. The adducts obtained are referred to as blocked isocyanates if they are less thermally stable than the products of the crosslinking reaction subsequently to be carried out. On exposure to heat, the blocking agent is eliminated and the polyisocyanate forms the more thermally stable bond, with crosslinking.

This principle is described in, for example, Vieweg-Höchlen, Kunststoff-Handbuch, volume VII, Polyurethane (Carl-Hanser-Verlag, Munich, 1966), page 11 et seq., and also forms the basis of a number of patents, e.g. German Published Applications Nos. DAS 2,640,295, DAS 2,612,638 and DAS 2,639,491 and EPA No. 0 000 060.

Such formulations have technical and economic disadvantages as a result of the eliminated blocking agent, which, when it remains in the crosslinked material, may have an adverse effect on the quality and, if it is volatile, presents emission problems. Routes to single-component systems free of blocking agents are described in German Laid-Open Applications Nos. DOS 3,112,054, DOS 3,228,670, DOS 3,228,724, DOS 3,228,723 and DOS 3,230,757.

The concept underlying these patents comprises dispersing polyisocyanates, in particular solid polyisocyanates, in media capable of reacting with isocyanates, to give a product which is stable during storage, premature undesirable reaction of the isocyanate groups with the surrounding medium being prevented by virtue of the fact that the disperse isocyanates are deactivated at their surface or, as stated in German Laid-Open Application No. DOS 3,230,757, possess retarded reactivity. The basic concept is the same in each case.

This deactivation or retardation is achieved if the surfaces of the isocyanate particles are treated with less than the stoichiometric amount, based on the total content of isocyanate, of a deactivating agent.

A large number of suitable substances are mentioned as deactivating agents, particularly suitable substances being those which react with isocyanates to give urea or polyureas.

In the patents listed, the purpose of using the stated deactivating polyisocyanates, which form stable dispersions in media capable of reacting with the isocyanate groups, is to provide single-component isocyanate systems, i.e. after elimination of the deactivation, the isocyanates are intended to react with the reactive substances in which they are dispersed and thus to form the desired end products, e.g. coatings, adhesive bonds or materials.

To achieve this objective in a simple and elegant manner, in the stated patents the deactivating or retarding reactions are preferably carried out in situ, i.e. in the media which are suitable for producing the desired end products and capable of reacting with isocyanates. In this case, the isocyanate and the medium capable of reacting with the isocyanate are used in suitable ratios of equivalents. This is always readily feasible if these media, for example polyhydroxy compounds or sluggishly reacting, sterically hindered amines, react with the isocyanates more slowly than do the rapidly reacting amine compounds, which have been suggested as preferred stabilizers.

If deactivation of the isocyanates is carried out externally in a low-viscosity medium, for example in cyclohexane with ethylenediamine or acetone/water, where the water serves as a deactivating reagent which forms urea structures and as a reaction medium (German Laid-Open Application No. DOS 3,112,054) or in water, the stabilized isocyanate is generally isolated by filtration, if necessary carefully dried, and mixed in the isolated, finely powdered form with the desired (polyol) starting materials for the single-component polyurethane reactive mixtures.

After deactivation of the polyisocyanates in low viscosity media, these deactivated polyisocyanates are used, as described in the stated patents, to obtain chemically stable dispersions directly in media capable of reacting with isocyanates or indirectly after isolation of the deactivated polyisocyanates.

In the deactivation in acetone/water, for example, evolution of gas is no longer observed after some time since in this case, according to German Laid-Open Application No. DOS 3,228,670, the deactivating reaction comes to a stop after the disperse isocyanate phase has been coated with the deactivating urea structures formed from water and from isocyanate groups present on the isocyanate particles.

However, the physical stability of such dispersions of deactivated isocyanate in low-viscosity media is unsatisfactory. The dispersions settle out, presumably because of the higher specific gravity of the isocyanates and their heterogeneous particle size distribution of, for example, from 0.1 to 200 μm.

However, low-viscosity, chemically and physically stable, possibly highly concentrated dispersions of deactivated polyisocyanates in organic solvents and/or water are of great interest, especially because such dispersions do not contain any directly available free isocyanate. This would be very advantageous, making for relatively safe handling, and would open up a number of novel applications for the crosslinking of isocyanates.

There would also be great advantages with regard to storage and stockpiling, since these dispersions of stabilized isocyanates could be stored without special measures to exclude atmospheric moisture.

The present invention describes routes to such advantageous dispersions, which are chemically and physically stable dispersions of polyisocyanates in low-viscosity media.

The present invention relates to a process for the preparation of stable dispersions of finely divided polyisocyanates in a liquid which may or may not contain surfactants, protective colloids and other assistants, by treating a polyisocyanate with one or more stabilizers in the presence or absence of the liquid, wherein the polyisocyanate dispersed in the liquid and treated with stabilizers is finely dispersed or milled under the action of high sheaf forces, if necessary with the addition of further stabilizer.

Particularly advantageously used polyisocyanates are those which are solid at room temperature.

Suitable liquids are both liquid substances which are inert to isocyanate groups and liquid substances capable of reacting with isocyanate groups, or a mixture of the two types of substances. Water or an aqueous solvent mixture may also be used as the liquid.

Preferred stabilizers are polyamidoamines.

The present invention furthermore relates to a process for the preparation of heat-crosslinkable isocyanate systems, wherein the stable dispersions of finely divided polyisocyanates, which dispersions are prepared by the novel process, are used as crosslinking agents.

Polyisocyanate dispersions which are chemically and physically stable at room temperature and storage temperatures up to about 60° C. can be obtained according to the invention, the polyisocyanate being dispersed, in the form of discrete particles which are deactivated on their surface, in media which are reactive and/or inert toward isocyanates. The dispersions are preferably subjected, in the presence of wetting agents and/or protective colloids, to a subsequent milling or subsequent dispersing procedure which controls the particle size.

Stabilization of the polyisocyanates is carried out according to the invention in general by applying a type of polymer shell. This polymer shell is formed from the isocyanate groups attached to the surface of the polyisocyanate particles and one or more compounds capable of reacting with isocyanate groups, only a minor amount, i.e. from 0.01 to 30, preferably from 0.1 to 5% of the total amount of isocyanate groups present being consumed.

For the purposes of the present invention, the compounds which form the polymer shell and are capable of reacting with isocyanates are referred to as stabilizers.

The polymer shell may be formed in situ, i.e. in the dispersion itself, or externally, i.e. in a liquid medium which may be the same as or may differ from, that subsequently used in the dispersion, or directly, for example by applying the stabilizer to solid, finely powdered polyisocyanates in a suitable mixer.

The deactivated polyisocyanates provided with the polymer shell and exhibiting a retarded reactivity may also be referred to as stabilized polyisocyanates.

The stabilized polyisocyanate should be present in the dispersion in as high a concentration as possible. The medium in which the stabilized polyisocyanate is dispersed is a liquid. This may be a low-viscosity liquid incapable of reacting with isocyanates, and/or a low-viscosity liquid capable of reacting with isocyanates. If this liquid can react with isocyanates or contains fractions capable of reacting with isocyanates, the stabilized polyisocyanate should be dispersed in amounts such that it is present substantially in excess of the stoichiometric amount, since, according to the invention, it is intended to make available substances which externally appear isocyanate-free and can be used for a variety of applications in the same way as free isocyanates, without having the disadvantages and dangers associated with handling of free isocyanates, for example health hazards and only a short shelf life (pot life) of the ready-to-use formulations.

According to the invention, the dispersions are finely dispersed and/or milled under the action of high shear forces; these steps may be carried out in particular in the presence of surfactants and/or viscosity regulators and/or other assistants, and correspond to a subsequent dispersing step or subsequent milling step which controls the particle size.

This after-treatment makes it possible to provide physically and chemically stable dispersions, i.e. dispersions which, even when stored for a long time, maintain their content of free isocyanate at a constant level and form no sediment or only loose sediment which can easily be stirred up again.

A surprising aspect, and one not suggested by the prior art, is the possibility of carrying out this after treatment with high-power dispersing apparatuses, e.g. stirred ball mills or dissolvers, even in media capable of reacting with isocyanates, e.g. water or water-containing mixtures, without the isocyanates reacting with these media to more than only a slight extent.

A technical prejudice against this method of obtaining dispersions which are chemically and physically stable, even in polar media, on prolonged storage is built up in, for example, German Laid-Open Application No. DOS 3,230,757, since this publication expressly mentions the use of shear forces or the addition of polar solvents for destroying such dispersions.

In the process according to the invention, the liquid serving as the dispersing medium may contain surfactants, protective colloids and other assistants, e.g. catalysts.

The substances employed for the preparation of the dispersion are described in detail below. Where lists of substances are used to describe them, these are intended to define the classes of substances used, without restricting the invention to the use of the substances listed.

Suitable polyisocyanates for the novel process are all di- or polyisocyanates or any mixtures of these, provided that they have a melting point above 10° C., preferably above 40° C., particularly preferably above 80° C.

These may be aliphatic, cycloaliphatic, araliphatic or, preferably, aromatic and heterocyclic polyisocyanates, or polyphenyl-polymethylene-polyisocyanates, obtained by aniline/formaldehyde condensation followed by phosgenation, according to British Pat. Nos. 874,430 and 848,671, as well as perchlorinated arylpolyisocyanates, carbodi- imide-containing polyisocyanates, allophanate-containing polyisocyanates, isocyanurate-containing polyisocyanates, urethane-containing or urea-containing polyisocyanates, polyisocyanates containing acylated urea groups, biuret containing polyisocyanates, polyisocyanates prepared by telomerization reactions, ester-containing polyisocyanates, and preferably uretdione-containing diisocyanates and urea containing diisocyanates. Examples of suitable polyisocyanates of this type are:

| | |
|---|---|
| p-xylylene diisocyanate | Mp.: 45–46° C. |
| 1,5-diisocyanatomethylnaphthalene | 88–89° C. |
| 1,3-phenylene diisocyanate | 51° C. |
| 1,4-phenylene diisocyanate | 94–96° C. |
| 1-methylbenzene 2,5-diisocyanate | 39° C. |
| 1,3-dimethylbenzene 4,6-diisocyanate | 70–71° C. |
| 1,4-dimethylbenzene 2,5-diisocyanate | 76° C. |
| 1-nitrobenzene 2,5-diisocyanate | 59–61° C. |
| 1,4-dichlorobenzene 2,5-diisocyanate | 134–137° C. |
| 1-methoxybenzene 2,4-diisocyanate | 75° C. |
| 1-methoxybenzene 2,5-diisocyanate | 89° C. |
| 1,3-dimethoxybenzene 4,6-diisocyanate | 125° C. |
| azobenzene 4,4'-diisocyanate | 158–161° C. |
| diphenyl ether 4,4'-diisocyanate | 66–68° C. |
| diphenylmethane 4,4'-diisocyanate | 42° C. |
| diphenyldimethylmethane 4,4'-diisocyanate | 92° C. |
| naphthalene 1,5-diisocyanate | 130–132° C. |

According to the invention, 1,5-naphthalene diisocyanate, 3,3'-diisocyanato-4,4'-dimethyl-N,N'-diphenylurea, dimeric 1-methyl-2,4-diisocyanatobenzene, dimeric 4,4'-diisocyanatodiphenylmethane and 3,3'-dimethyl-4,4'-diisocyanatodiphenyl are particularly preferably used.

Examples of suitable stabilizers for these polyisocyanates are the substances stated in German Laid-Open Applications Nos. DOS 3,112,054, DOS 3,228,670, DOS 3,228,723 and DOS 3,230,757. These are compounds which produce a sort of polymer shell on the surface of the polyisocyanate particles. Preferably used stabilizers are those which form this polymer shell by reacting selectively with the isocyanate groups on the surface of the particles. As a result of this reactive stabilization, the polymer shell is bonded firmly to the polyisocyanate particles without substantial proportions of the total amount of isocyanate groups present being consumed. The isocyanate consumption is in general from 0.01 to 30, preferably from 0.01 to 10, particularly preferably from 0.01 to 5%.

Examples of useful stabilizers are compounds possessing hydroxyl, carboxyl, phenolic hydroxyl, amide or mercaptan groups.

Reactions which lead to urea or polyurea structures on the isocyanates are also particularly useful for deactivating the isocyanate groups on the surface of the polyisocyanate particles, i.e. for stabilizing the isocyanate dispersions, because the said structures are insoluble in most polyols and organic solvents. Urea forming or polyurea-forming reagents of this type are water and primary or secondary amines.

An advantage of this process is that the urea structures react further with other isocyanates at elevated temperatures to form biuret structures, i.e. the deactivating agent is incorporated in the crosslinked system during subsequent use and does not leave behind any inhomogeneity.

Suitable amine stabilizers for the stated polyisocyanates are bifunctional or polyfunctional, low molecular weight or high molecular weight compounds possessing aliphatically bonded, primary and/or secondary amino groups and/or terminal —CO-NH-NH$_2$ groups and/or hydrazines and having a molecular weight of from 32 to about 60000, preferably from 60 to 3000. These are, for example, low molecular weight and/or high molecular weight primary and/or secondary polyamines, preferably diamines. The amino groups are in general bonded to aliphatic groups, cycloaliphatic groups or the aliphatic radical of araliphatic groups. Hydrazine (generally in the form of hydrazine hydrate) or alkyl-substituted hydrazines, such as N,N'-dimethylhydrazine, may also be used. Other suitable amine stabilizers are compounds possessing terminal hydrazine groups, e.g. dihydrazides, such as oxalic dihydrazide, adipic dihydrazide or terephthalic dihydrazide, and compounds possessing hydrazide and semicarbazide, carbazate or amino groups, e.g. β-semicarbazidoalanyl hydrazide, 2-semicarbazidoethylene carbazate, aminoacetic hydrazide, β-aminopropionic hydrazide or ethylene-bis-carbazate or ethylene-bis-semicarbazide. Polyhydrazides which are obtained by hydrazinolysis of polyacrylates and whose preparation is described, for example, by M. Hartmann, R. Dowbenko and U.T. Hockswender in Organic Coating +Applied Polymer Science 46 (1982), 429–432 are also very useful. However, aliphatic or cycloaliphatic diand polyamines which, in addition to the amino groups, may furthermore possess OH, tertiary amino, ether, thioether, urethane or urea groups are preferred. Examples of di- and polyamines which can be used according to the invention are ethylenediamine, 1,2- and 1,3-propanediamine, 1,4-butanediamine, 1,6-hexanediamine, neopentanediamine, 2,2,4- and 2,4,4-trimethyl-1,6-diaminohexane, 2,5-dimethyl2,5-diaminohexane, 1,10-decanediamine, 1,11-undecanediamine, 1,12-dodecanediamine, bis-aminomethyl-hexahydro4,7-methano-indane (TCD-diamine), 1,3-cyclohexanediamine, 1,4-cyclohexanediamine, 1-amino-3,3,5-trimethyl-5-aminomethylcyclohexane (isophoronediamine), 2,4- and/or 2,6-hexahydrotoluylenediamine, 2,4'- and 4,4'-diaminodicyclohexylmethane, m- and p-xylylenediamine, bis-(3-aminopropyl)methylamine, bis-N,N'-(3-aminopropyl)-piperazine, diaminoperhydroanthrazenes and 1-amino-2-aminomethyl-3,3,5-(3,5,5)-trimethylcyclopentane, 2,2-dialkylpentene-1,5-diamines and triamines such as 1,5,11-triaminoundecane, 4-aminomethyl-1,8-diaminooctane, lysine methyl ester, cycloaliphatic triamines according to German Laid-Open Application DOS 2,614,244, 4,7-dioxadecane-1,10-diamine, 2,4- and 2,6-diamino-3,5-diethyl-1-methylcyclohexane and mixtures of these, alkylated diaminodicyclohexylmethanes, e.g. 3,3'-dimethyl-5,5'-diaminodicyclohexylmethane and 3,5-diisopropyl-3',5'-diethyl-4,4'-diaminodicyclohexylmethane, perhydrogenated diaminonaphthalenes, perhydrogenated diaminoanthrazenes and higher-valent amines, such as diethylenetriamine, triethylenetetramine, pentaethylenehexamine, dipropylenetriamine, tripropylenetetramine or N,N'-dimethylethylenediamine, 2,5-dimethylpiperazine, 2-methylpiperazine, piperazine (hydrate) and 2-hydroxyethylpiperazine.

Apart from these low molecular weight diamines, or as a mixture with them, it is also possible to use higher molecular weight diamines and polyamines, such as those obtained, for example, by amination of polyoxyalkylene glycols with ammonia by the method described in Belgian Pat. No. 634,741 or U.S. Pat. No. 3,654,370. Other fairly high molecular weight polyoxyalkylenepolyamines can be prepared by the methods listed in the company publication entitled Jeffamine, Polyoxypropylene Amines from Texaco Chemical Company, 1978, for example by hydrogenating cyanoethylated polyoxypropylene glycols (German Laid-Open Application No. DOS 1,193,671), by aminating polypropyleneglycolsulfonic acid esters (U.S. Pat. No. 3,236,895), by treating a polyoxyalkylene glycol with epichlorohydrin and a primary amine (French Pat. No. 1,466,708) or by reacting NCO prepolymers with hydroxyl-containing enamines, aldimines or ketimines and hydrolyzing the product, as described in German Laid-Open Application No. DOS 2,546,536. Other suitable higher molecular weight di- and polyamines are the polyamines which are accessible by the methods described in German Laid-Open Applications No. DOS 2,948,419 and DOS 3,039,600, via the carbamate stage, by alkaline hydrolysis of NCO prepolymers with bases. Other very useful higher molecular weight polyamines are the substances which are prepared by polycondensation of polycarboxylic acids, e.g. polymeric linseed oil fatty acid, with an excess of diamines and triamines and are available, for example, as Versamide ® from Schering AG. These higher molecular weight polyamines have molecular weights of about 400–6000, preferably 400–3000. Because of their composition, such higher molecular weight polyamines are particularly useful for producing a non-brittle, resilient polyurea shell. They are therefore employed, preferably as a mixture with the low molecular weight di- and polyamine compounds, as amine stabilizers for the polyisocyanate particles. Of course, any combinations of the stated amine, hydrazine and hydrazide stabilizers may be used in order, for example, to balance disadvantageous side effects of one amine by corresponding advantages of other amines (for example, low molecular weight and high molecular weight diamines used in combination) or in order to combine as many advantageous side effects as possible. Examples of suitable combinations are combinations of rapidly reacting amines, e.g. ethylenediamine, with amines slowed down by steric hindrance, or combinations of low molecular amines or hydrazines with high molecular weight amines, e.g. aliphatic aminopolyethers.

In order to control and acclerate the deactivation, catalysts may also be added. Preferred catalysts are those which selectively accelerate the deactivation. However, the deactivation catalysts may be identical to the catalysts which subsequently accelerate or control the intended heat-activated reaction.

The liquid, i.e. the dispersing liquid medium, may be reactive and/or inert toward isocyanate groups. Since it is the object of the present invention to provide isocyanate crosslinking agents for a large number of applications, the novel stable dispersions should have a very high content of available isocyanate. It is therefore advantageous if the selected dispersing media which are reactive toward isocyanate groups possess a very high equivalent weight.

Examples of suitable liquid media are low-molecular weight and/or high molecular weight mono- and/or polyols and/or aromatic polyamines, preferably those having molecular weights from 60 to 6000. Other examples are fairly long-chain alcohols, such as isohexyldecanol, and propoxylation products of monohydric alcohols having molecular weights of, preferably, from 400 to 6000, e.g. propoxylation products of n-butanol. Examples of suitable low molecular weight polyols are ethylene glycol, N-methyldiethanolamine, castor oil, polyethylene glycol ethers having a molecular weight of from 400 to 6000, ethoxylation or propoxylation products of low molecular weight di- and polyols having molecular weights of from 400 to 6000, propoxylated trimethylolpropane, propoxylated ethylenediamine, linear or branched polypropylene glycol ethers which may contain proportionate amounts of ethylene oxide randomly distributed, arranged in blocks or present as terminal groups and have molecular weights of from 400 to 6000. Propoxylation products of ethylenediamine, e.g. a tetraalcohol of ethylenediamine and propylene oxide, are also suitable.

Other useful substances are the liquid compounds which are usually employed for the preparation of polyurethane plastics and are reactive toward isocyanates. Examples of these are polyethers, polythioethers, polyacetals, polycarbonates, polylactones, polyesteramides or polyesters possessing two or more hydroxyl groups, as well as polybutadiene compounds. Polyethers and polyesters are particularly preferred.

Suitable polyethers are those of the conventional type, which may be prepared, for example, by polymerization of tetrahydrofuran or of epoxides such as ethylene oxide, propylene oxide, butylene oxide, styrene oxide or epichlorohydrin, or by means of an addition reaction of these epoxide compounds, preferably ethylene oxide or propylene oxide, with water, diamines and low molecular weight diols and triols.

Polyesters which are obtained by condensation of polyols with polycarboxylic acids, polycarboxylic anhydrides or polycarboxylic esters are also suitable. Polyesters obtained from lactones, e.g. ϵ-caprolactone, or hydroxycarboxylic acids, e.g. ω-hydroxycaproic acid, can also be employed.

Polyacetals, for example the compounds which can be prepared from glycols and formaldehyde, are also useful.

Suitable hydroxyl-containing polycarbonates are those of the conventional type, for example those which can be prepared by reacting propane-1,3-diol, butane-1,4-diol and/or hexane-1,6-diol, di-, tri- or tetraethylene glycol or thiodiglycol with a diaryl carbonate, e.g. diphenyl carbonate, or phosgene.

Liquid polybutadienes containing terminal hydroxyl groups are also suitable according to the invention, as are copolymers of olefinically unsaturated monomers without active hydrogen atoms, and olefinically unsaturated monomers possessing active hydrogen.

Polyhydroxy compounds modified with vinyl polymers and as obtained, for example, by polymerization of styrene and acrylonitrile in the presence of polyethers or polycarbonate-polyols, are also useful liquids for the novel process.

Other typical examples of the stated compounds to be used are described in detail in High Polymers Vol. XVI, Polyurethanes, Chemistry and Technology, editor Saunders Frisch, Interscience Publishers, New York, London, Volume I, 1962, pages 32–42 and pages 44–54, and volume II, 1964, pages 5-6 and 198-199, and in Kunststoff-Handbuch, volume VII, Vieweg-Höchtlen, Carl-Hanser-Verlag, Munich, 1966, for example on pages 45-71, and in German Laid-Open Application No. DOS 2,854,384.

It is of course possible to use mixtures of the above polyhydroxy compounds, in the presence or absence of nonpolar or slightly polar solvents based on aliphatic, cycloaliphatic or aromatic hydrocarbons, halohydrocarbons, ethers, alcohols, ketones or esters and/or water.

Plasticizer-type compounds, e.g. phthalates, such as dioctyl, diisododecyl, dibenzyl or butyl benzylphthalate, or phosphates such as trioctyl phosphate, may also be used as the liquid medium for stabilizing the polyisocyanates. Hydrocarbons, such as butadiene oils, or polyethers having a fairly high molecular weight can also be employed as the reaction medium. The use of extenders and/or solvents which are not capable of reacting with isocyanates also makes it possible to regulate the equivalent weight of the dispersions. It is also possible to use only the stated solvents and/or water.

Some of the substances which can be used as the liquid medium also have a stabilizing effect. In such cases, it is possible to dispense with a further stabilizer. This is the case, for example, with some dispersions in water or water/solvent mixtures. In such cases, the stabilizing reaction ceases after the polymer shell has formed.

The surfactants preferably used in the after-treatment to control particle size are conventional anionic, cationic or neutral surfactants, e.g. sorbitan fatty acid esters, polyoxyethylene sorbitan fatty acid esters, arylsulfonates, alkali metal salts of higher fatty acids, oxyethylated oleylamine, sulfosuccinates, soyabean lecithin, polyethylene oxide fatty acid esters, polypropylene oxide fatty acid esters and decynediol derivatives. Condensates of phenolsulfonic acids, urea and formaldehyde, as described in German Pat. Nos. 1,113,457 and 2,327,579, are particularly useful.

Of course, not all the stated surfactants are effective in every dispersion; furthermore, a number of other surfactants not listed here are also useful. The choice of a suitable combination is determined by the particular case, and is familiar to the skilled worker.

Examples of other assistants, which may or may not be useful, are antiskinning agents, antifoams and especially viscosity regulators, such as cellulose esters, methylcellulose, ethylcellulose, polymeric acids and salts of polymeric acids, natural and synthetic polysaccharides and prttein products, after-treated starch, polyureas, for example as described in German Laid-Open Applications Nos. DOS 2,359,929 and DOS 2,360,019, and polyarylamides, polyvinyl alcohols, polyvinyl ethers, etc.

Heating the novel dispersions of finely divided polyisocyanates eliminates their retardation or deactivation.

The novel dispersions can therefore very advantageously be employed for formulating heat-crosslinkable isocyanate systems, suitable reactants being the conventional ones, such as polyetherpolyols, polyesterpolyols, hydroxyl-containing polymers and other substances which are reactive toward isocyanate groups, in the presence or absence of low molecular weight chain extenders possessing hydroxyl and/or amino groups.

The temperature required for the crosslinking reaction depends on the reactivity of the reactants and on any catalysts present. It is in general from 70° to 180° C., preferably from 90° to 150° C.

Suitable units for producing high shear forces for the novel fine dispersing or milling procedure are those known from milling and dispersing technology, e.g. stirred ball mills, bead mills, sand mills, ball mills, slot mills, high-speed dissolvers or dispersing apparatuses of the rotor/stator type.

The novel dispersing or milling procedure in the presence of substances which are reactive toward isocyanate is advantageously carried out at temperatures below the reaction temperature of the particular mixture of substances used, preferably at from 0° to 60° C., in particular from 10° to 40° C.

The Examples which follow describe possible novel processes for the preparation of dispersions and compositions, without restricting the invention to the stated examples of processes and compositions. Other suitable compositions and processes can be easily derived from the detailed description of the inventive concept.

In the Examples, parts and percentages are by weight.

EXAMPLE 1

500 parts of a polyetherpolyol based on glycerol and propylene oxide and having a molecular weight of about 4000 are initially taken in a cooled planetary mixer.

750 parts of toluylene diisocyanate dimerized via uretdione groups (TDI-U) are added, and the mixture is kneaded to a smooth paste at 22°–26° C. in the course of 3 minutes.

22.5 parts of a polyamidoamine having an amine number of about 400 (Euretek, from Schering) are added, and mixed in over a further 5 minutes; thereafter, 22.5 parts of soya bean lecithin and 22.5 parts of polyoxyethylene sorbitan trioleate are mixed in (3 minutes) and 825 parts of water are stirred in.

An inhomogeneous dispersion with a pronounced tendency to settle out is formed.

This dispersion is after-treated in a high-speed disperser of the rotor/stator type (Ultra-Turrax) to give a homogeneous low-viscosity dispersion which, after a few days, forms a little loose sediment which can easily be stirred up. The chemical stability is defined by checking the free isocyanate content. (The analytical method does not detect the isocyanate groups blocked in the uretdione bond.)

| Isocyanate content after manufacture | 8.2% |
|---|---|
| Isocyanate content after 24 hours | 8.0% |
| Isocyanate content after 3 days | 8.1% |
| Isocyanate content after 7 days | 8.1% |
| Isocyanate content after 30 days | 8.1%. |

EXAMPLE 2a 600 parts of TDI-U (cf. Example 1) and 400 parts of isopropanol are converted to a suspension in the course of 3 minutes using a high-speed disk stirrer. Thereafter, 15 parts of Euretek (cf. Example 1) are stirred in over 3 minutes; a dispersion which shows a pronounced tendency to settle out but is chemically stable is produced.

EXAMPLE 2b

The dispersion from Example 2a is mixed with 800 parts of 1% strength solution of the ammonium salt of a copolymer of 60 parts of styrene, 10 parts of acrylic acid and 30 parts of maleic anhydride, using a high-speed disk stirrer. The result is a dispersion which shows a pronounced tendency to settle out and forms very compact sediment which is difficult to stir up.

EXAMPLE 2c The dispersion from Example 2b is further milled in a cooled open stirred ball mill at 20°-26° C. for 15 minutes. The result is a chemically and physically stable dispersion which, even after prolonged standing, forms only loose sediment which can easily be stirred up.

EXAMPLE 3a 4500 parts of water and
165 parts of Euretek (cf. Example 1) are dissolved in a dissolver.
5500 parts of TDI-U are added, and dispersed for 4 minutes. The result is a dispersion which shows a pronounced tendency to settle out and forms compact sediment which is difficult to stir up.

EXAMPLE 3b 1272 parts of water,
4 parts of a polysaccharide having a high molecular weight (e.g. Kelzan®) and
117 parts of a condensate of phenolsulfonic acid, urea and formaldehyde (as described in German Pat. No. 2,327,579) are dissolved,
2500 parts of the dispersion described in Example 3a are added, and the mixture is then further dispersed by milling for 20 minutes in a cooled open stirred ball mill. This further dispersing greatly reduces the mean particle size and gives a narrower particle size distribution (cf. Figure). The subsequent milling does not significantly reduce the isocyanate content of the dispersion. In determining the isocyanate content, the blank value due to the assistants should be taken into account.

After about 2 weeks, the dispersion forms a little loose sediment which can very easily be stirred up, and the isocyanate content remains stable.

Isocyanate content:

| Isocyanate content | |
|---|---|
| prior to dispersing | 10.8% |
| after dispersing | 9.6% |
| after 1 week | 9.6% |
| after 6 weeks | 9.5%. |

EXAMPLE 4

400 parts of flaky diphenylmethanediisocyanate are comminuted in a mortar to give a coarse powder, which is stirred into a solution of
27.5 parts of Euretek (cf. Example 1),
4 parts of high molecular weight polysaccharide (e.g. Kelzan) and
4 parts of polyoxyethylene sorbitan trioleate in
762 parts of water, after which the mixture is dispersed for 5 minutes using an Ultra-Turrax. The temperature is kept at <20° C. by cooling. The result is a stable dispersion having a content of 9.81% of free isocyanate.

EXAMPLE 5a 500 parts of TDI-U (cf. Example 1) are mixed with a solution of
15 parts of Euretek (cf. Example 1) in
30 parts of xylene for 1 hour in an open laboratory kneader to give a loose powder.
20 parts of polyoxyethylene sorbitan trioleate are then added, and mixing is continued for a further hour. The result is a loose powder.

EXAMPLE 5b 100 parts of stabilized polyisocyanate from Example 5a and
250 parts of a polyetherpolyol based on an adduct of water and propylene oxide and having a molecular weight of about 2000 are dispersed under severe conditions, using a high-speed dissolver, in the course of 10 minutes. The temperature is kept at <30° C. by cooling. The result is a readily flowing paste which, after 2 weeks, forms only a very small amount of sediment which can easily be stirred up.

EXAMPLE 5c 100 parts of stabilized polyisocyanate from Example 5a, 270 parts of water and
10 parts of a high molecular weight polysaccharide (e.g. Kelzan) are dispersed under severe conditions using an Ultra-Turrax in the course of 10 minutes. The temperature is kept at <40° C. by cooling. In the resulting readily flowing dispersion, the isocyanate content of 11.2% is found to be unchanged after 6 weeks.

We claim:

1. A process for the preparation of a stable dispersion of a finely divided solid polyisocyanate in a liquid which comprises: treating a solid polyisocyanate with one or more polyamines having molecular weights of 400–6000, and thereafter finely dispersing or milling the treated polyisocyanate in the liquid under the action of high-shear forces to form a stable dispersion of solid polyisocyanate in the liquid under the action of high-shear forces to form a stable dispersion of solid polyisocyanate particles containing a polymer shell formed by reaction of the polyamine with the surface of the particles, said reaction consuming from 0.01 to 30% of the total isocyanate groups in the particles.

2. The process of claim 1, wherein from 0.1 to 5% of the isocyanate groups are consumed in the reaction.

3. The process of claim 1, wherein further polyamine is added to the liquid when the treated polyisocyanate is being subjected to high-shear forces.

4. The process of claim 1, wherein assistants selected from the group consisting of surfactants, protective colloids or mixtures thereof are added to the liquids.

5. The process of claim 1, wherein the liquid used is a liquid substance which is inert toward isocyanate groups.

6. The process of claim 1, wherein the liquid used is a liquid substance which is capable of reacting with isocyanate groups, or a mixture of this substance with a liquid substance which is inert toward isocyanate groups.

7. The process of claim 1, wherein the liquid used is water or an aqueous solvent mixture.

8. A process as claimed in claim 1, wherein the plyamine used is a polyamidoamine.

* * * * *